(12) United States Patent
Juncker et al.

(10) Patent No.: US 10,300,485 B2
(45) Date of Patent: May 28, 2019

(54) NANOARRAY-IN-MICROARRAY MULTIPLEXED ANALYSIS METHODS AND SYSTEMS

(71) Applicant: THE ROYAL INSTITUTION FOR THE ADVANCEMENT OF LEARNING/MCGILL UNIVERSITY, Montreal (CA)

(72) Inventors: David Juncker, Verdun (CA); Gina Zhou, Montreal (CA); Sebastien Bergeron, Chambly (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 2 days.

(21) Appl. No.: 15/332,650

(22) Filed: Oct. 24, 2016

(65) Prior Publication Data

US 2017/0116733 A1    Apr. 27, 2017

Related U.S. Application Data

(60) Provisional application No. 62/245,575, filed on Oct. 23, 2015.

(51) Int. Cl.
*B01L 3/00* (2006.01)
*G01N 21/64* (2006.01)
(Continued)

(52) U.S. Cl.
CPC ........ *B01L 3/5085* (2013.01); *G01N 21/6452* (2013.01); *G06T 5/004* (2013.01);
(Continued)

(58) Field of Classification Search
None
See application file for complete search history.

(56) References Cited

U.S. PATENT DOCUMENTS 4,647,524 A    3/1987 Sullivan
4,840,714 A    6/1989 Littlehales
(Continued)

FOREIGN PATENT DOCUMENTS

WO    2008157640    12/2008
WO    2009137521    11/2009
WO    2010111265     9/2010

OTHER PUBLICATIONS

Zhou et al., "Digitizing immunoassay on an antibody nanoarray to improve assay sensitivity," 2013 Transducers Eurosensors XXVII 17th Int. Conf. Solid-State Sensors Actuators Microsystems Transducers Eurosensors 2013, No. Jun., pp. 2783-2786, 2013.*

(Continued)

*Primary Examiner* — Soo Shin
(74) *Attorney, Agent, or Firm* — Norton Rose Fulbright Canada

(57) ABSTRACT

Methods and apparatuses for performing a nanoarray-in-microarray assay is provided, which can be used to estimate a protein concentration in a sample solution. A plurality of nanodots are fabricated on a surface having at least one affinity binder. One or more microspots are superimposed over the nanodots on predetermined regions of the surface, each of the microspots comprising at least one antibody. An assay process is performed on the surface, and the surface is imaged to acquire optical images of the nanodots within each microspot. Image analysis algorithms are the performed on the optical images to identify bindings on individual ones of the plurality of nanodots.

20 Claims, 16 Drawing Sheets

(51) Int. Cl.
*G06T 5/00* (2006.01)
*G06T 7/136* (2017.01)

(52) U.S. Cl.
CPC ....... *G06T 7/136* (2017.01); *B01J 2219/0074* (2013.01); *B01J 2219/00317* (2013.01); *B01J 2219/00385* (2013.01); *B01J 2219/00662* (2013.01); *B01J 2219/00702* (2013.01); *B01J 2219/00725* (2013.01); *B01L 2300/0636* (2013.01); *B01L 2300/0822* (2013.01); *G01N 21/648* (2013.01); *G01N 21/6458* (2013.01); *G06T 2207/10056* (2013.01); *G06T 2207/30242* (2013.01)

(56) References Cited

U.S. PATENT DOCUMENTS

| | | | |
|---|---|---|---|
| 7,235,307 | B2 | 6/2007 | Chen et al. |
| 9,366,668 | B2* | 6/2016 | Rao ............... B01J 19/0046 |
| 2003/0108949 | A1* | 6/2003 | Bao ............... B01J 19/0046 435/7.1 |
| 2006/0159916 | A1* | 7/2006 | Dubrow ........... B01J 20/28007 428/357 |
| 2007/0184494 | A1* | 8/2007 | McBride .......... B01D 61/00 435/7.9 |
| 2009/0048120 | A1* | 2/2009 | Park ............... G01Q 60/42 506/9 |
| 2010/0248993 | A1* | 9/2010 | Tserepi .......... B01J 19/0046 506/30 |
| 2011/0294703 | A1 | 12/2011 | Jeon et al. |
| 2012/0085894 | A1* | 4/2012 | Zhong ............. G01N 21/648 250/227.11 |

OTHER PUBLICATIONS

Ongo et al., "Ordered, Random, Monotonic and Non-Monotonic Digital Nanodot Gradients," PLoS One. 2014; 9(9): e106541.*
Søndergaard et al., "Facing the Design Challenges of Particle-Based Nanosensors for Metabolite Quantification in Living Cells," Chem. Rev., 2015, 115 (16), pp. 8344-8378.*
Zhou et al., "Digitizing immunoassay on an antibody nanoarray to improve assay sensitivity," 2013 Transducers Eurosensors XXVII 17th Int. Conf. Solid-State Sensors Actuators Microsystems Transducers Eurosensors 2013, No. June, pp. 2783-2786, 2013 (Year: 2013).*
Ongo et al., "Ordered, Random, Monotonic and Non-Monotonic Digital Nanodot Gradients," PLoS One. 2014; 9(9): e106541 (Year: 2014).*
Søndergaard et al., "Facing the Design Challenges of Particle-Based Nanosensors for Metabolite Quantification in Living Cells," Chem. Rev., 2015, 115 (16), pp. 8344-8378 (Year: 2015).*
Han et al., "Ultrasensitive On-Chip Immunoassays with a Nanoparticle-Assembled Photonic Crystal," ACS Nano, vol. 6, No. 10, pp. 8570-8582, 2012 (Year: 2012).*
Seo et al., "A Three-Dimensional Nanostructured Array of Protein Nanoparticles," Adv. Funct. Mater. 2010, 20, 4055-4061 (Year: 2010).*
J.M.K. Ng et al., Components for Integrated Poly (dimethylsiloxane) Microfluidic Systems .Electrophoresis, vol. 23, pp. 3461-3473.
L. Gervais et al., Toward One-Step Point-of-Care Immunodiagnostics using Capillary-Driven Microfluidics and PDMS Substrates, Lab on a Chip, vol. 9, pp. 3330-3337.
R.A. George et al., Ceramic Capillaries for use in Microarray Fabrication, Genome Res., vol. 11, pp. 1780-1783.
R. Safavieh et al., Straight SU-8 Pins, J. Micromechanics and Microengineering, vol. 20, 055001, 2010.
H. Li et al., Hydrogel Droplet Microarrays with Trapped Antibody-Functionalized Beads for Multiplexed Protein Analysis 4, Lab on a Chip, vol. 11, pp. 528-534.

M. Pia-Roca et al., Addressable Nanowell Arrays Formed Using Reversibly Sealable Hybrid Elastomer-Metal Stencils, Anal. Chem., vol. 82, pp. 3848-3855.
C. Steinert et al., TopSpotTM Vario: A Novel Microarrayer System for Highly Flexible and Highly Parallel Picoliter Dispensing, Biomed. Microdevices, vol. 11, 755-761.
W. Du et al., SlipChip, Lab on a Chip, vol. 9, 2286-2292.
Du and W. Liu et al., SlipChip for Immunoassays in Nanolitre Volumes, Anal. Chem., vol. 82, pp. 3276-3282.
M.Y. Lee et al., Metabolizing Enzyme Toxicology Assay Chip, MetaChip for High-Throughput Microscale Toxicity Analyses, Proc. Natl. Acad. Sci. U. S. A., vol. 102, pp. 983-987.
T.G. Fernandes et al., Three-Dimensional Cell Culture Microarray for High-Throughput Studies of Stem Cell Fate, Biotechnol and Bioeng., vol. 106, pp. 106-118.
M-Y. Lee et al., 5 Three-dimensional Cellular Microarray for High-Throughput Toxicology Assays, Proc. Natl. Acad. Sci. U. S. A, vol. 105, pp. 59-63.
Wu et al., A Sandwiched Microarray Platform for Benchtop Cell-Based High Throughput Screening, Biomaterials, vol. 32, pp. 841-848.
Kwong et al., Drug-Eluting Microarrays for Cell-Based Screening of Chemical-Induced Apoptosis, Anal. Chem., vol. 83, pp. 4118-4125.
Bilang-Bleuel et al., Intrastriatal injection of an adenoviral vector expressing glial-cell-line-derived neurotrophic factor prevents dopaminergic neuron degeneration and behavioral impairment in a rat model of Parkinson disease, Proc. Natl. Acad. Sci. USA, vol. 94, pp. 8818-8823, Aug. 1997, Neurobiology.
Murari et al. —Wireless Multichannel Integrated Potentiostat for Distributed Neurotransmitter Sensing, Proceedings of the 2005 IEEE Engineering in Medicine and Biology 27th Annual Conference Shanghai, China, Sep. 1-4, 2005, pp. 7329-7332.
M. Kuwata et aL., Sliding Micro Valve Injection Device for Quantitative Nano Liter Volume, 8 the Int. Conf. Miniaturized Systems for Chemistry and Life Sciences, 2004, pp. 342-344.
R. Briard et al., Crack Bridging Mechanism for Glass Strengthening by Organosilane Water-based Coatings, J. Non-Cryst. Solids, vol. 351, pp. 323-330.
Mandel et al., Midbrain injection of recombinant adeno-associated virus encoding rat glial cell line-derived neurotrophic factor protects nigral neurons in a progressive 6-hydroxydopamine-induced degeneration model of Parkinson's disease in rats, Proc. Natl. Acad. Sci. USA, vol. 94, pp. 14083-14088, Dec. 1997, Neurobiology, pp. 14083-14087.
Akerud et al., Neuroprotection through Delivery of Glial Cell Line-Derived Neurotrophic Factor by Neural Stem Cells in a Mouse Model of Parkinson's Disease, The Journal of Neuroscience, Oct. 15, 2001, 21(20) pp. 8108-8118.
J.W. Findlay et al., Appropriate Calibration Curve Filling in Ligand Binding Assays, AAPS Journal, vol. 9, pp. E260-E267.
Kearns et al., GDNF Protection against 6-OHDA: Time Dependence and Requirement for Protein Synthesis, The Journal of Neuroscience, Sep. 15, 1997, 17(18) pp. 7111-7118.
C. Pfleger et al., Effect of serum content and diluent selection on assay sensitivity and signal intensity in multiplex bead-based immunoassays, vol. 329, pp. 214-218.
Rutkowski et al., Cytokine Serum Levels in Soft Tissue Sarcoma Patients: Correlations with Clinico-Pathological Features and Prognosis, Int. J. Cancer, vol. 100, pp. 463-471.
S. Fiorilli et al. Vapor-Phase Self-Assembled Monolayers of Aminosilane on Plasma-Activated Sillicon Substrates, J. Colloid and Interface Science, vol. 321, pp. 235-241.
F. Zhang et al., Chemical Vapor Deposition of Three Aminosilanes on Si licon Dioxide: Surface Characterization, Stability, Effects of Silane Concentration, and Cyanine Dye Adsorption, Langmuir, vol. 26(18), pp. 14648-14654.
Rascol et al., A Five-Year Study of the Incidence of Dyskinesia in Patients With Early Parkinson's Disease Who Were Treated With Ropinirole or Levodopa, The New England Journal of Medicine, May 18, 2000, pp. 1484-1491.

(56) References Cited

OTHER PUBLICATIONS

Kong et al., Serum HER-2 concentration in patients with primary breast cancer, pp. 373-376, http://jcp.bmj.com/ on May 27, 2016—Published by group.bmj.com.

Takahashi et al, Association of Serum Endoglin with Metastasis in Patients with Colorectal, Breast, and Other Solid Tumors, and Suppressive Effect of Chemotherapy on the Serum Endoglin, Clinical Cancer Research , vol. 7, 524-532, Mar. 2001.

Aliustaoglu et al., Preoperative serum leptin levels in patients with breast cancer, Med. Oncol. (2010) 27 pp. 388-391.

Bramwell et al, Serial Plasma Osteopontin Levels Have Prognostic Value in Metastatic Breast Cancer, Clin Cancer Res, 2006;12(11) Jun. 1, 2006, pp. 3337-3343.

Poustinchi et al. Low Power Noise Immune Circuit for Implantable CMOS Neurochemical Sensor Applied in Neural Prosthetics, Proceedings of the 5th International IEEE EMBS Conference on Neural Engineering Cancun, Mexico, Apr. 27-May 1, 2011, pp. 695-699.

Scholl et al, Circulating levels of the macrophage colony stimulating factor CSF-1 in primary and metastatic breast cancer patients. A pilot study., Breast Cancer Research and Treatment 39: 275-283, 1996. Kluwer Academic Publishers. Printed in the Netherlands.

Kim et al, The multiplex bead array approach to identifying serum biomarkers associated with breast cancer, http://breast-cancer-research.com/content/11/2/R22.

Yurkovetsky et al, Multiplex Analysis of Serum Cytokines inMelanoma Patients Treated with Interferon-A2b, Clin Cancer Res 2007;13(8) Apr. 15, 2007, pp. 2422-2428.

ENZ—Circuit Techniques for Reducing the Effects of Op-Amp Imperfections: Autozeroing, Correlated Double Sampling, and Chopper Stabilization, Proceedings of the IEEE, vol. 84, No. 11, Nov. 1996, pp. 1584-1614.

Pla-Roca et al., Antibody Colocalization Microarray: A Scalable Technology for Multiplex Protein Analysis in Complex Samples, Molecular & Cellular Proteomics, vol. 11, pp. 1-12.

Y. Cai et al., Channel-Free Shear Driven Circular Liquid Chromatography, Lab on a Chip, vol. 8, pp. 1784-1786. The "SlipChip".

G. Desmet et al.. The Possibility of Generating High-Speed Shear-Driven Flows and Their Potential Application in Liquid Chromatography, Anal. Chem., vol. 72, pp. 2160-2165.

Dose Response to Intraventricular Glial Cell Line-Derived Neurotrophic Factor Administration in Parkinsonian Monkeys1 Zhiming Zhang,2 Yasuyuki Miyoshi,2 Paul A. Lapchak,4 Frank Collins,4 Dana Hilt,5 Carl Lebel,6 Richard Kryscio3 and Don M. Gash2 Anatomy and Neurobiology, University of Kentucky Medical Center, Lexington, Kentucky Accepted for publication May 2, 1997.

Robinson et al., Detecting Subsecond Dopamine Release with Fast-Scan Cyclic Voltammetry in Vivo, Clinical Chemistry 49:10, pp. 1763-1773 (2003).

\* cited by examiner

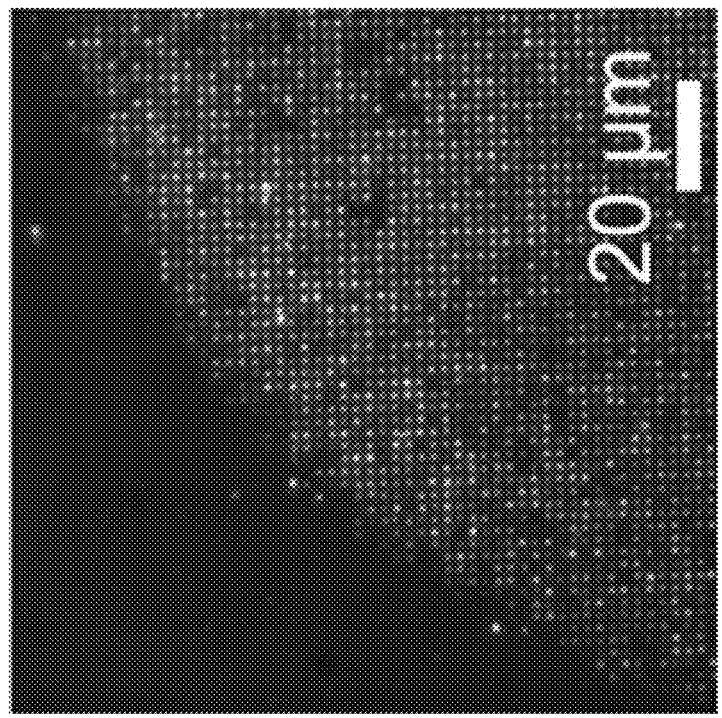
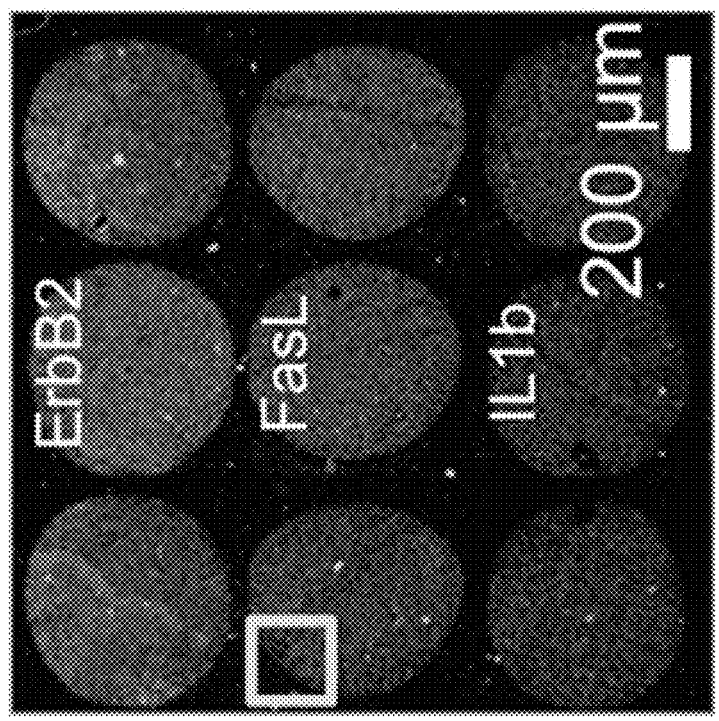
FIGURE 7A
FIGURE 7B

NANOARRAY-IN-MICROARRAY MULTIPLEXED ANALYSIS METHODS AND SYSTEMS

CROSS-REFERENCE TO RELATED APPLICATIONS

This application claims priority under 35 U.S.C. 119(e) of U.S. Provisional Application 62/245,575, entitled "Nanoarray-in-Microarray Multiplexed Analysis Methods and Systems", filed 2015 Oct. 23, the contents of which are incorporated herein by reference.

TECHNICAL FIELD

This present disclosure relates generally to biological assays, and more particularly to reducing the noise within such assays through digital nanoarrays and nanoarray within microarray multiplexing.

BACKGROUND

The early diagnosis of disease can significantly impact the outcome for a patient as well as significantly reduce the costs of treatment and care. The diagnosis of diseases at the earliest stages requires ultra-sensitive, multiplex assays. The sensitivity of an assay is limited by the noise within the assay. In biological assays, noise tends to arise primarily from non-specific binding (NSB), wherein both non-targeted low-affinity molecules present at high abundance and the targeted molecules at low abundance bind to the background surface. This results in fluctuations in the background measurements thereby compromising the assay sensitivity. Within the prior art microarray assays and digital assays are two of the most promising technologies exploited today. Whilst antibody microarrays offer high density analysis with low sample volumes their sensitivity is inadequate for early detection. In contrast, whilst digital assays can reach single molecule resolution they completely lack, or have limited, multiplexing capabilities and hence are not easily scaled for large-scale protein analysis. However, irrespective of these tradeoffs, neither technology addresses NSB.

Accordingly, it would be beneficial to provide assays that simultaneously provide high assay sensitivity, multiplicity and noise rejection in a single platform.

SUMMARY OF THE INVENTION

There is accordingly provided a method for performing a nanoarray-in-microarray assay, comprising: fabricating a plurality of nanodots on a surface having at least one affinity binder; superimposing at least one microspot over the nanodots on predetermined regions of the surface, each of the at least one microspot comprising at least one antibody of a plurality of antibodies; performing an assay process on the surface; acquiring at least one optical image of the nanodots within each microspot; and performing an image analysis on the at least one optical image to identify bindings on individual ones of the plurality of nanodots.

In some embodiments, the predetermined regions of the array of nanodots are defined by blocking the surface to define a predetermined number of regions with predetermined geometry.

In some embodiments, blocking the surface comprises applying at least one aptamer having a predetermined number of modified base pairs.

In some embodiments, fabricating the plurality of nanodots comprises nano-contact printing the plurality of nanodots.

In some embodiments, superimposing the at least one microspot comprises inkjet spotting the at least one microspot.

In some embodiments, the nanodots are configured to perform spatial rejection of non-specific bindings via the image analysis.

In some embodiments, performing the assay process comprises performing at least one of: a silver-enhanced sandwich immunoassay process; and an immunoassay process employed at least one of a fluorescent marker and a photoluminescent marker.

In some embodiments, performing an image analysis comprises: generating a low frequency content image from the acquired optical image; subtracting the low frequency content image from the optical image to generate a normalized image; fitting a 2D Gaussian at the centre of each of a plurality of spots in the normalized image; applying a spot mask to extract data relating to the plurality of spots; and extracting an intensity reading for a plurality of nanodots within the optical image based on the plurality of spots.

In some embodiments, performing an image analysis further comprises: establishing a threshold within the extracted intensity readings; and counting a nanodots with an intensity reading meeting a predetermined condition with respect to the threshold as instances of a binding occurrence.

According to another broad aspect, there is provided an assay device, comprising a detection surface having defined thereon a plurality of nanodots each having at least one affinity binder; and at least one microspot superimposed over the nanodots on predetermined regions of the detection surface, each of the at least one microspots comprising at least one antibody of a plurality of antibodies.

In some embodiments, the assay device further comprises at least one aptamer applied to the detection surface to define the predetermined regions with predetermined geometry, the at least one aptamer having a predetermined number of modified base pairs.

In some embodiments, the plurality of nanodots are fabricated by nano-contact printing.

In some embodiments, the at least one microspot is fabricated by inkjet spotting.

In some embodiments, the nanodots are configured to perform spatial rejection of non-specific bindings as part of an image analysis process.

In some embodiments, a spacing between the plurality of nanodots is 2 µm.

In some embodiments, a diameter of the microspot is between 100 µm and 800 µm.

According to another broad aspect, there is provided a method for estimating a protein concentration in a sample solution, comprising: immobilizing capture antibodies mixed with fluorescently-labeled detection antibodies on a microarray slide by nano-contact printing; performing a sandwich assay by sequentially incubating the sample solution with the fluorescently-labelled detection antibodies; imaging results of the assay to acquire a plurality of two-colour fluorescent images; overlaying the acquired two-colour fluorescent images to reveal at least one co-localized spot; and performing an image analysis algorithm to count the co-localized spots to estimate the protein concentration.

In some embodiments, performing a sandwich assay comprises performing a silver-enhanced sandwich immunoassay.

In some embodiments, imaging the results of the assay comprises imaging the assay with a total internal reflection fluorescent microscope.

In some embodiments, performing an image analysis algorithm comprises revealing bindings under a dark field microscope.

It is an object of the present disclosure to mitigate limitations in the prior art relating to biological assays and more particularly to reducing the noise within such assays through digital nanoarrays and nanoarray within microarray multiplexing.

In accordance with an embodiment of the present disclosure there is provided an assay method with integrated noise rejection from non-specific binding based upon spatial exclusion.

In accordance with an embodiment of the invention there is provided a device for performing a biological assay providing noise rejection of noise arising from non-specific binding within the measurements by spatial exclusion.

In accordance with an embodiment of the invention, there is provided an assay method with integrated quality control that allows for statistical noise rejection of non-specific binding occurring on the nanoarray.

In accordance with an embodiment of the invention there is provided an assay method exploiting a detection surface comprising a pattern of nanostructured elements disposed within a pattern of microstructures, wherein the detection surface allows for execution of a multiplexed digital assay process with noise reduction of noise arising from non-specific binding within the measurements by spatial exclusion.

In accordance with an embodiment of the invention there is provided a device for performing an assay, comprising a detection surface comprising a pattern of nanostructured elements disposed within a pattern of microstructures, wherein the detection surface allows for execution of a multiplexed digital assay process with noise reduction of noise arising from non-specific binding within the measurements by spatial exclusion.

In accordance with an embodiment of the invention there is provided a method comprising: fabricating a plurality of nanodots upon a substrate comprising at least an affinity binder; fabricating microspots which are superimposed upon predetermined regions of the plurality of nanodots, each microspot comprising at least an antibody of a plurality of antibodies; performing an assay process; acquiring optical imaging of the nanodots within each microspot; and performing image analysis on the one or more optical images to identify reveal bindings on single nanodots.

In accordance with an embodiment of the invention there is provided a method comprising: fabricating a plurality of nanodots upon a substrate comprising at least an affinity binder; performing an assay process; acquiring optical imaging of the nanodots; and performing image analysis on the one or more optical images to identify reveal bindings on single nanodots.

In accordance with an embodiment of the invention there is provided an assay method exploiting a detection surface comprising a pattern of surface bound biomolecules, wherein the detection surface allows for execution of a multiplexed digital assay process with noise reduction of noise arising from non-specific binding within the measurements by spatial exclusion and the surface bound biomolecules are antibodies.

In accordance with an embodiment of the invention there is provided a device for performing an assay, comprising a detection surface comprising a pattern of surface bound biomolecules, wherein the detection surface allows for execution of a multiplexed digital assay process with noise reduction of noise arising from non-specific binding within the measurements by spatial exclusion.

In accordance with an embodiment of the invention there is provided a device for performing an assay, comprising a detection surface comprising a pattern of nanostructured elements disposed within a pattern of microstructures, wherein the detection surface allows for execution of a multiplexed digital assay process with noise reduction of noise arising from non-specific binding within the measurements by spatial exclusion; and the nanosized features on the device were used to capture, to detect, and to analyze single proteins or vesicles.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIGS. 7A-B are microspot images of an example sample;

DETAILED DESCRIPTION

The present disclosure is directed to biological assays and more particularly to reducing the noise within such assays through digital nanoarrays and nanoarray within microarray multiplexing.

1.A. Noise Rejection Mechanism

As discussed supra suppression of noise from non-specific binding is an important element of achieving high sensitivity within an assay. Accordingly, a noise rejection methodology is provided to address at least in part non-specific binding (NSB). The noise rejection methodology is compatible with integration with assays based upon spatial exclusion. Additionally, an assay technology that spatially discriminates non-specific binding, with digital nanoarray (DNR) assays exploiting spatial discrimination of non-specific binding as a noise rejection mechanism is provided, as well as assays that provide nanoarray-in-microarray (NAiMA) surfaces to realize multiplexing allowing for scaling from a few times to hundreds of times, which can scale beyond the demonstrated the 16-plex up to 1000 s based on a scaling law. Moreover, automated inspection and measurement techniques allowing signal extraction in both singleplex and multiplex arrays upon optical inspection for such assays is provided, including systems with image capture and image analysis algorithms for signal extraction for operator independence and high throughput, automated testing, and/or inspection.

Figure 1A:
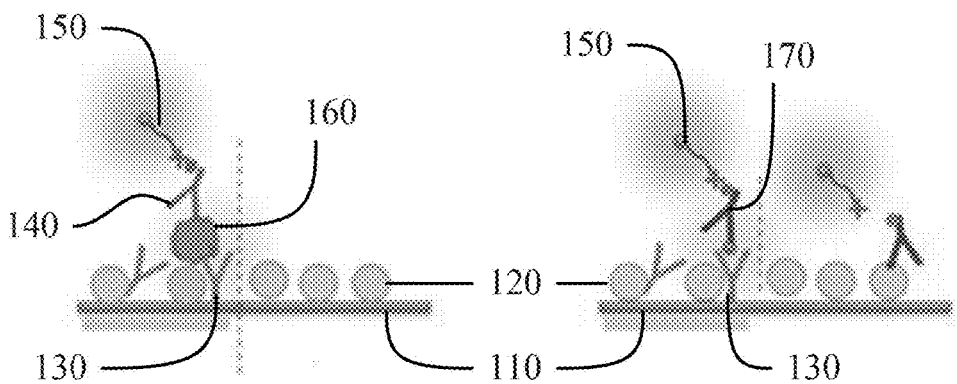
FIGS. 1A-D depict a design binding sequence according to an embodiment of the invention and three non-specific binding scenarios.

With reference to FIGS. 1A-D, NSB is the binding of non-targeted molecules to the probe that remain on the surface after blocking and washing stages during an assay. NSB can be either sample driven (inherent to the sample) or reagent driven (reagents used in an assay) or a combination of the two. Thus, FIG. 1A illustrates an ideal binding scenario, where an assay 110 is provided with a plurality of nanodots 120 and interstitial areas between the nanodots 120. In the interstitial areas can be located capture antibodies 130. In the ideal binding scenario, a target protein 160 binds with one of the capture antibodies 130, and a streptavidin dye 150 binds to the target protein via a detection antibody 140. In certain embodiments, the detection antibodies 140 are biotinylated.

Figure 1B:
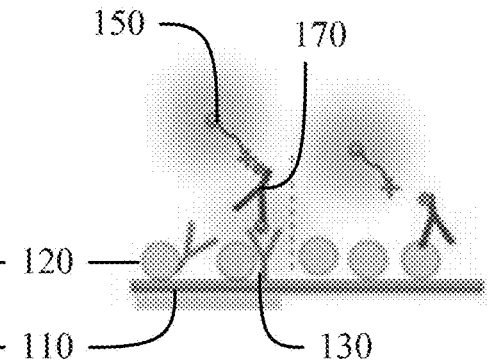
Figure 1C:
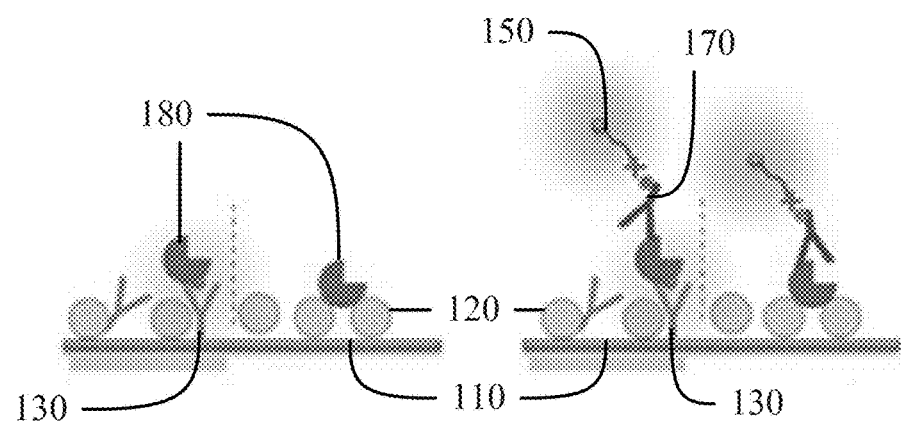
Figure 1D:
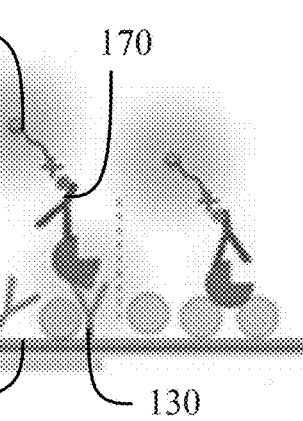

To demonstrate how this fraction surface may provide noise rejection, consider three possible NSB mechanisms depicted in FIGS. 1B-D. Let f be defined as a fraction of active binding surface over the total assay area. FIG. 1B illustrates reagent-driven NSB, whereby reagent molecules 170 falsely bind on the capture antibodies 130 with a probability of f. With this mechanism alone, the streptavidin dye 150 can bind to the reagent molecules 170, however fluorescently-labeled antibodies sticking outside of the dots are completely eliminated and excluded in the analysis. FIG. 1C illustrates sample-driven NSB, where sample molecules 180 can bind to the nanodots 120 and/or to the capture antibodies 130. The sample molecules 180 do not bind with the streptavidin dye 150, and thus do not emit fluorescent or photoluminescent optical signals, and hence often go undetected in an assay 110. Given that there are millions of nanodots 120 on the surface of an assay 110 then the number of falsely occupied sites is expected to be negligible. FIG. 1D illustrates the combined effect of reagent-driven NSB and sample-driven NSB. With the combined effect, interfering sample molecules 180 bind first and are subsequently recognized by reagent molecules 170, to which the streptavidin dye 150 can then also bind. The probability of an individual event happening is f and the combined probability is f assuming the two events are independent.

Taken together, the theoretical noise rejection rate can be estimated as $1-f-f^2$. The inventors have found f=1%=0.01 in certain embodiments, which in some cases can yield a noise rejection rate in excess of 99%, compared no noise rejection mechanism within prior art assay techniques.

In addition to spatial noise rejection, the nanoarray provides an integrated quality control by assessing the prevalence of non-specific binding. By measuring the amount of NSB to the passivated surface, an estimate of the signal from the nanoarray spots originating from NSB can be made. Provided the passivated surface and nanospot have similar chemistry, this estimate can used to correct the measured binding for chance NSB on the nanospot. This method extends the NSB noise rejection from just spatial based rejection to statistical NSB rejection as well.

The nanoarray can be made of any affinity binder, and can be combined with any surface passivation method. The surface passivation can be modified to closely match the chemistry of these affinity binders in order to provide statistical NSB noise rejection. An example of an embodiment of this method is to pattern a nanoarray of aptamers and to block with aptamers with a number of modified base pairs. As the chemistry of the two oligos would be very similar, the rate of NSB would be expected to be similar, providing us with the ability to differentiate the specific capture signal from the non-specific capture signal.

1.B Digital Nanoarray Assay (DNR) with Noise Rejection:

Using the noise rejection mechanism described above in Section 1.A, a low-cost nano-contact printing technique has been established and which can be used to fabricate large areas of nanodots. The nano-patterned assay 110 can be used in a classic sandwich assay, and the assay results imaged by Total Internal Reflection Fluorescence (TIRF) microscopy allowing detection down to single binding events on the nanosize binding surfaces.

Figure 2:
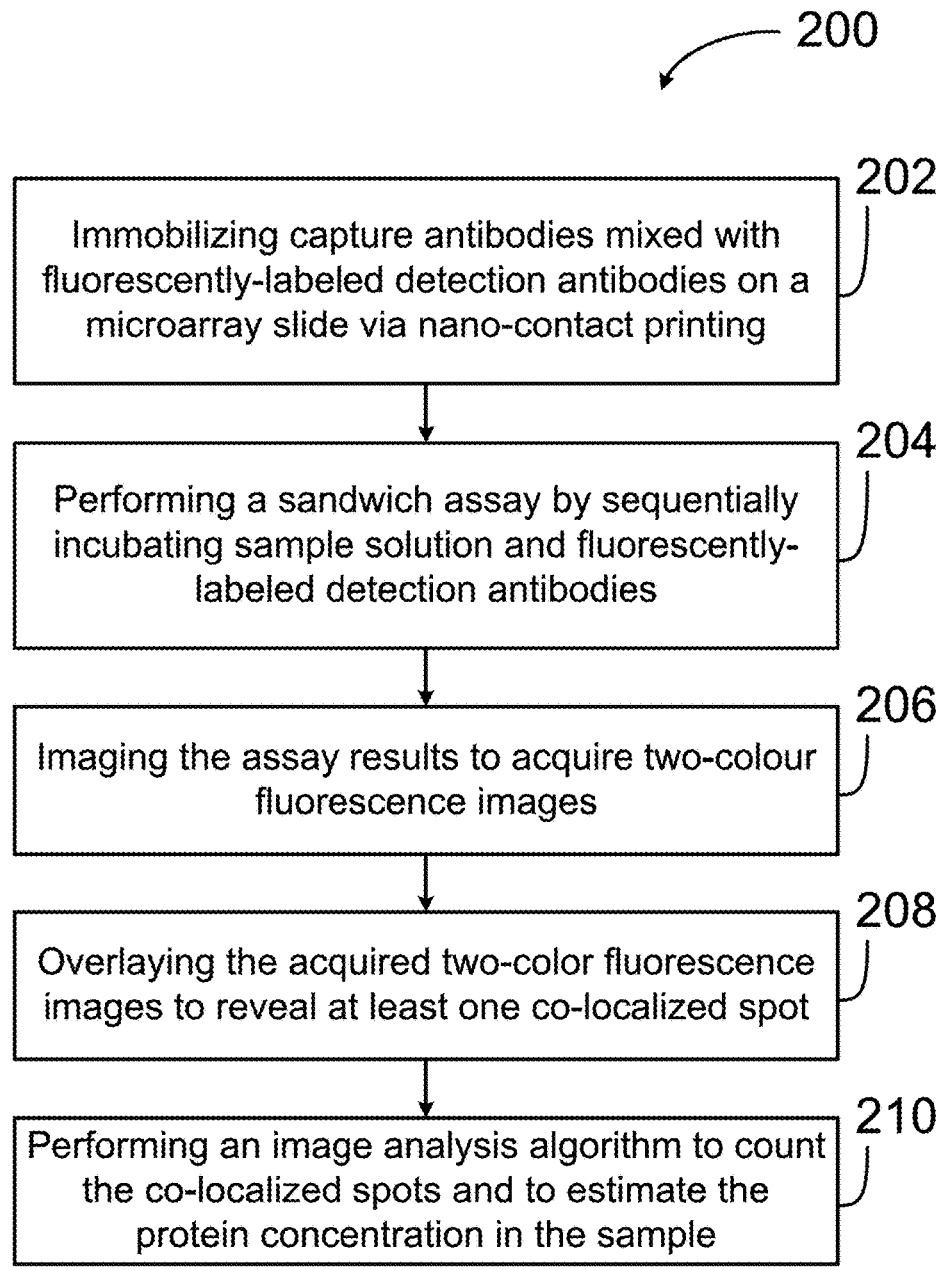
FIG. 2 is a flowchart illustrating a method for providing a digital assay according to an embodiment.

Accordingly, and with reference to FIG. 2, an example method 200 for estimating a protein concentration in a sample solution according to an embodiment of the invention is depicted. At step 202, capture antibodies mixed with fluorescently-labeled detection antibodies are immobilized on a microarray slide by nano-contact printing. The slide can be made of glass, for example. At step 204, a sandwich assay is performed by sequentially incubating a sample solution and the fluorescently-labeled detection antibodies. At step 206, the assay results are imaged using a TIRF microscope, or equivalent, to acquire two-colour fluorescence images. At step 208, the acquired two-color fluorescence images are overlaid to reveal the true binding signals, which are co-localized spots. At step 210, an image analysis algorithm is performed to count the co-localized spots and to estimate the protein concentration in the sample.

Figure 3A:
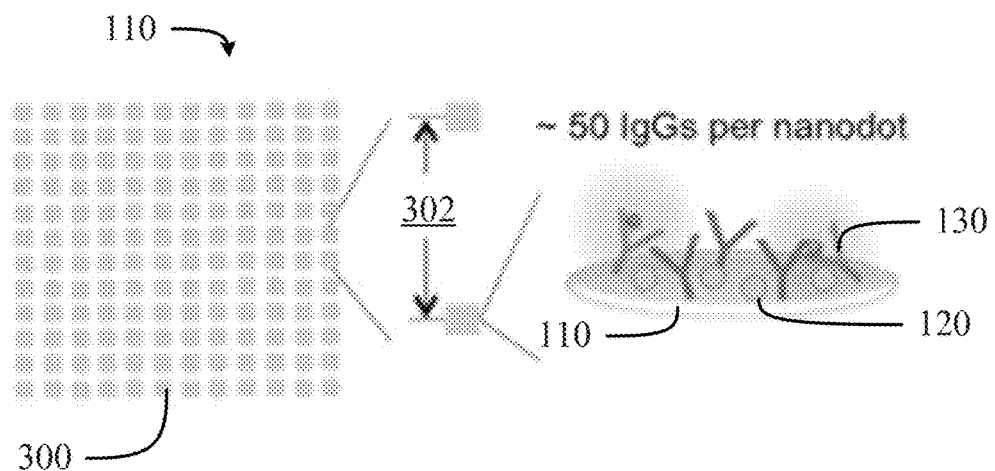
FIGS. 3A-F depict an example process flow for a digital assay and example images from experimental samples processed according to an embodiment of the invention.
Figure 3B:
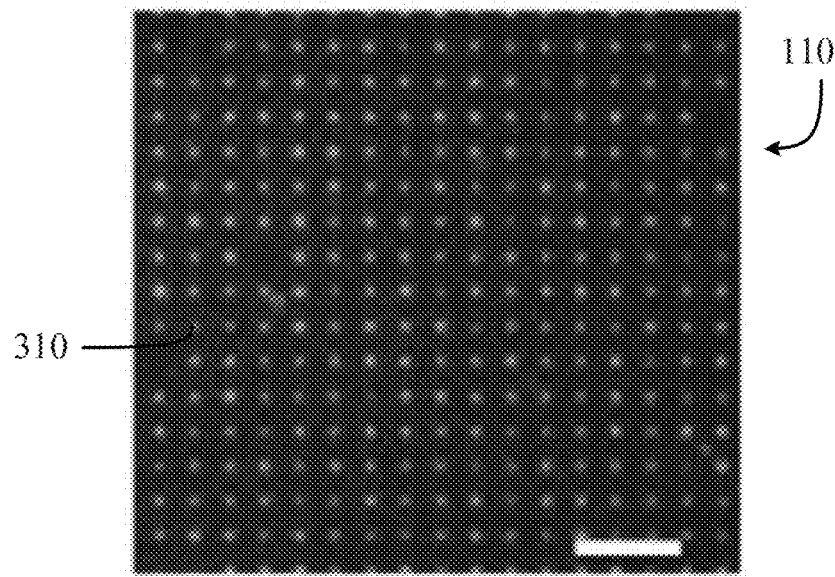
Figure 3C:
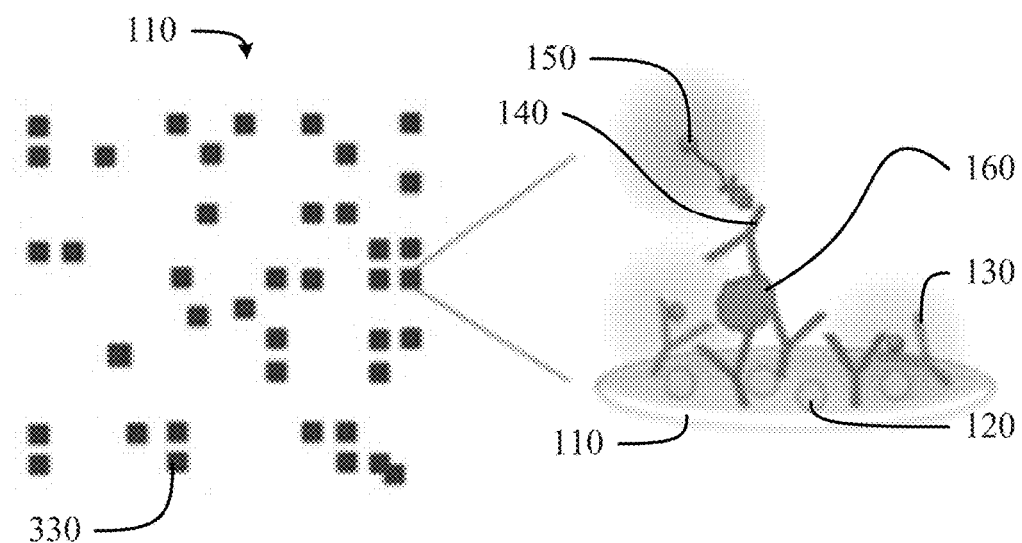
Figure 3D:
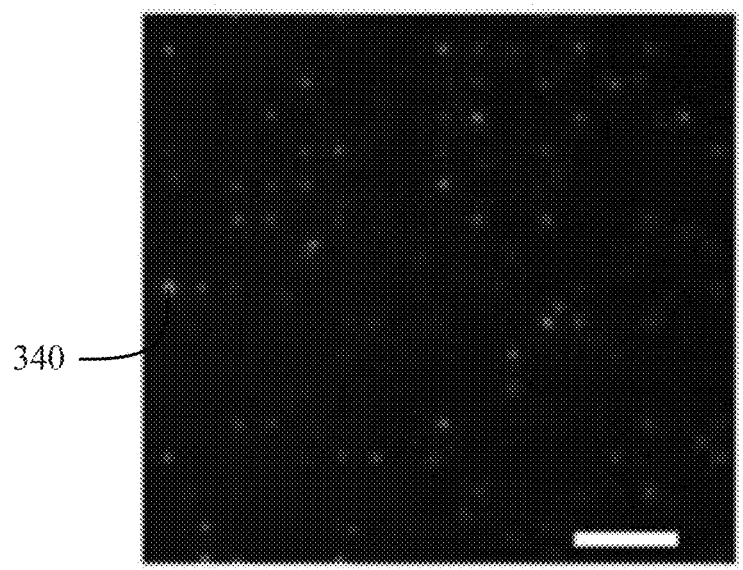
Figure 3E:
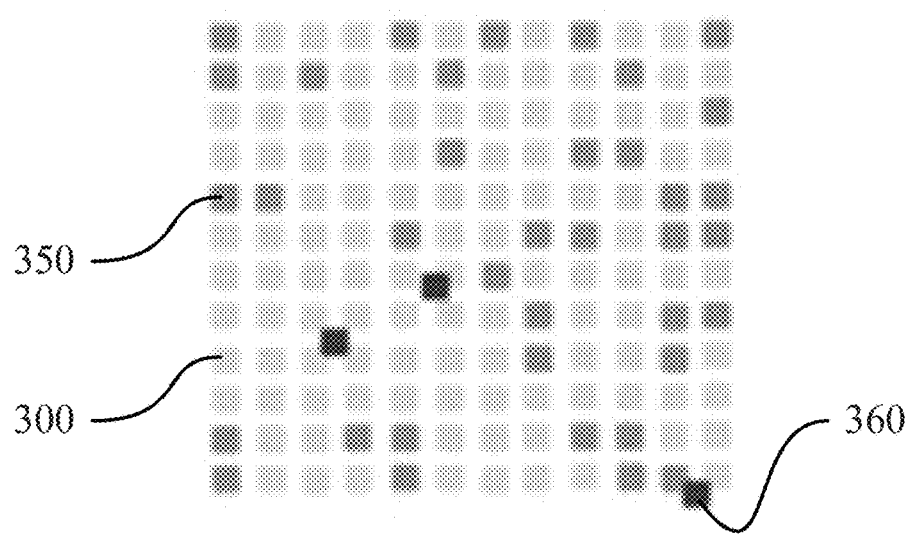
Figure 3F:
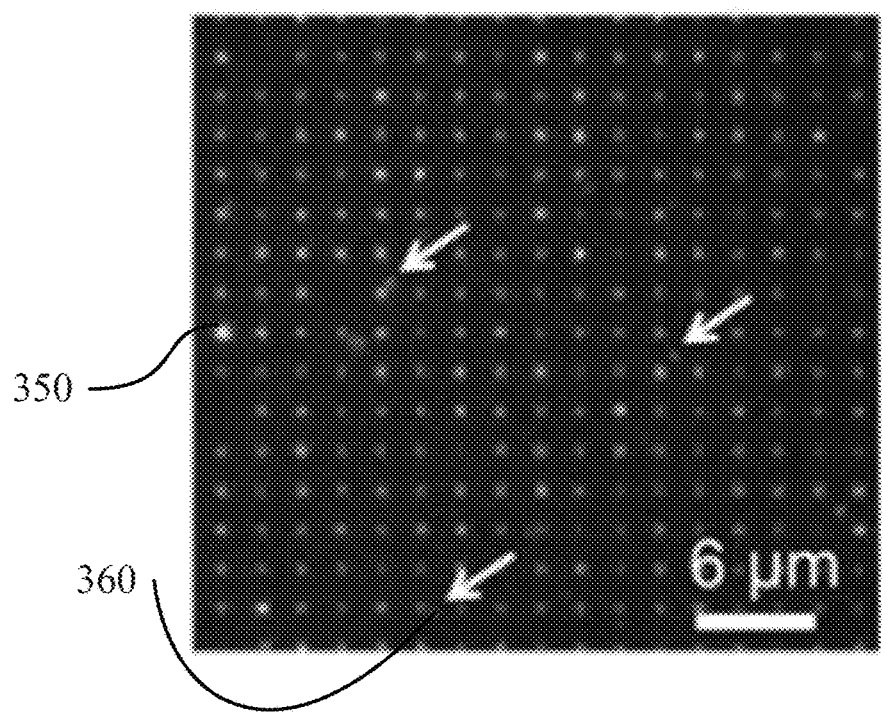

With reference to FIGS. 3A-F, the method 200 can also be illustrated visually. FIG. 3A shows the assay 110 having a plurality of nanoarray elements 300. Spacing 302 between elements 300 of the nanoarray can be, for example, 2 µm. FIG. 3B shows a two-colour fluorescence image showing the individual nano-dimensioned binding spots 310. FIG. 3C shows the assay 110 with incubated samples 330. FIG. 4D shows a two-colour fluorescence image showing the individual nano-dimensioned binding signals 340. FIG. 3E shows the overlain two-color fluorescence image, revealing the true binding signals 350 which are co-localized with the elements 300 of the microarray. Elements 360 which are located between the elements 300 of the microarray are excluded. With reference to FIG. 3F, elements 360 not co-localized, and thus excluded, are indicated by the arrows. In certain embodiments, a scale bar in FIGS. 3B, D, and F is 6 µm and a pitch is approximately 350 µm×350 µm.

The resulting assay 110 can detect, in certain embodiments, interleukin 1β at levels down to 30 attog/mL, more than 1000 times more sensitive than conventional fluorescence microarray assays. Accordingly, the patterned assay surface provides noise rejection so that NSB (i.e., the non-co-located elements 360) can be discriminated from the true binding signals 350 using, for example, imaging recognition software.

1.C. Scalable Multiplex Digital Assay on NAiMA:

Multiplexed digital assays combine the high density of a microarray with the noise rejection feature of a nanoarray as implemented according to an embodiment of the invention.

Figure 4:
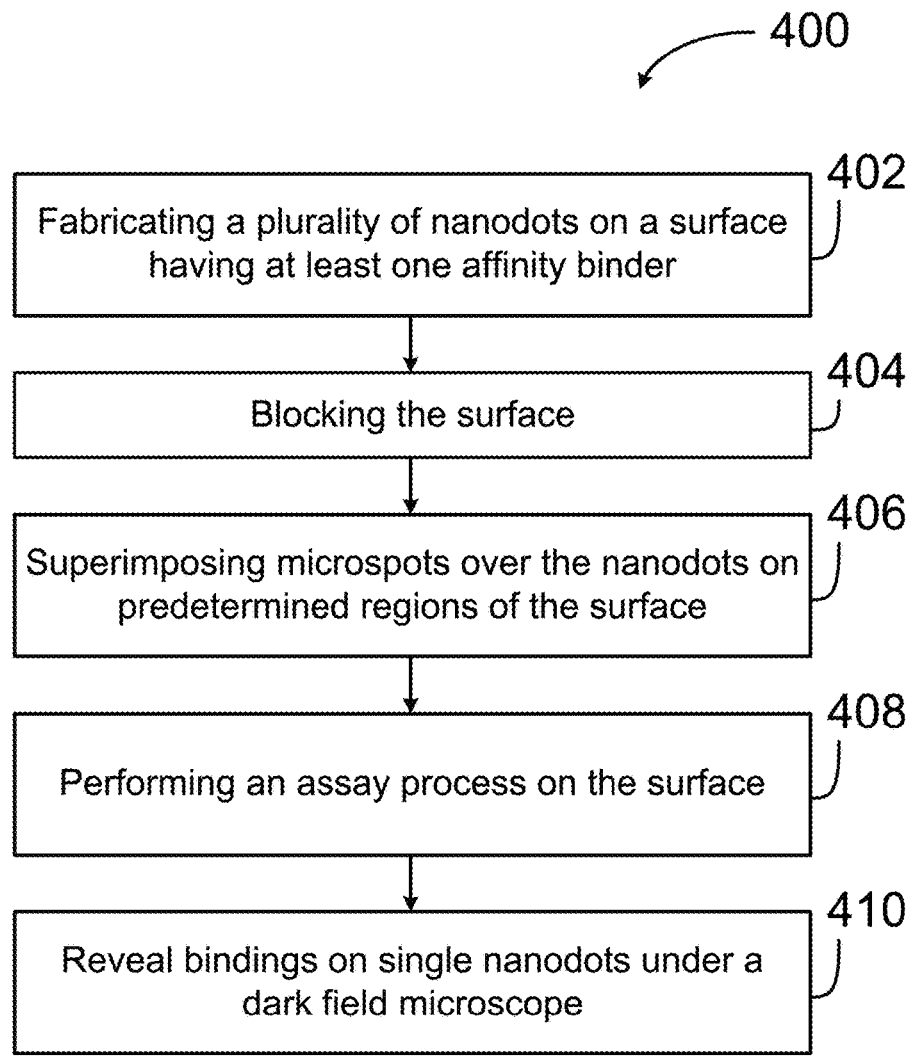
FIG. 4 is a flowchart illustrating a method for performing a nanoarray-in-microarray assay according to an embodiment.
Figure 5:
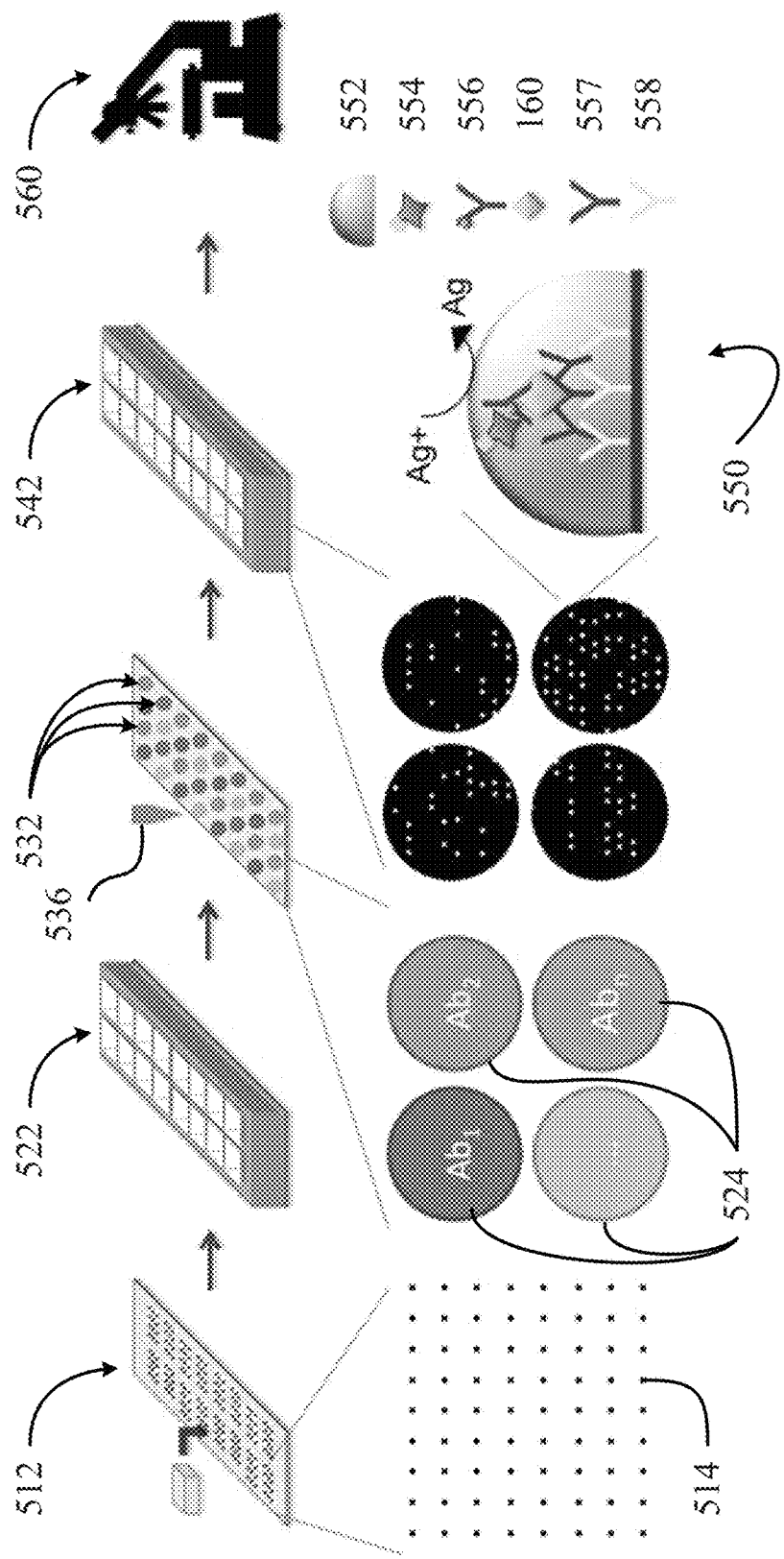
FIG. 5 depicts an example process flow for a multiplexed digital assay according to an embodiment of the invention.

With reference to FIGS. 4 and 5, a method 400 for producing the assay 110 is described. At step 402, a plurality of nanodots 514 are fabricated on a surface 512 having at least one affinity binder, for example using nano-contact printing. At step 404, the surface 512 is blocked, as shown in element 522, for example with aptamers 524 with a number of modified base pairs. At step 406, microspots 532 are superimposed over the nanodots 514 on predetermined regions of the surface 512. Each microspot 532 comprises at least one antibody of a plurality of antibodies, and can be applied, for example, using inkjet spotting 536. This provides the multiplexing functionality, hereinafter referred to as nanoarray-in-microarray (NAiMA).

At step 408, an assay process, for example silver-enhanced sandwich immunoassay (SENSIA) 542, is performed on the surface 512. At step 410, bindings 550 are revealed on single nanodots under a dark field microscope 560, or using any other suitable technique. In certain embodiments, the bindings 550 include a silver component 552 on which is located a GaM IgG+GaM-Cy3 element 558 and a M cAb element 557. The target protein 160 binds to these elements, and a G Biotin-dAb element 556 binds to the target protein 160. Additionally, a SA-HRP element 552 can bind to the G Biotin-dAb element 556.

A diameter of the microspots 532 can range from 100 μm≤φ≤800 μm by adjusting spotting volume, number of droplets, and printing buffer viscosity. However, it be noted that other dimensions may be employed without departing from the scope of the invention. The microspot size affects the microarray density (scale of the multiplexing) and the number of nanodots 514 that each microspot 532 covers (assay dynamic range) in an opposite manner. In certain embodiments, a single array of nanodots may be employed.

Figure 6:
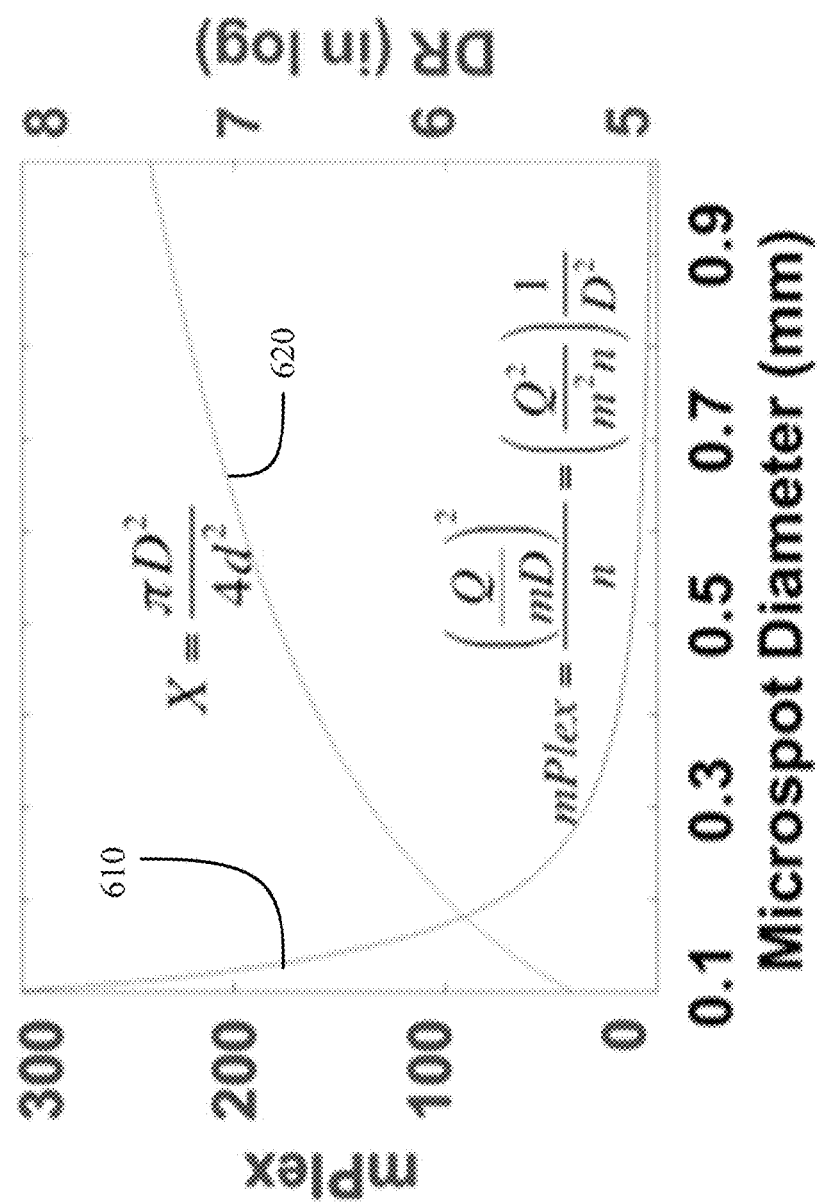
FIG. 6 is a graphical representation of a scaling law of microspot diameter and digital assay dynamic range.

With reference to FIG. 6, a scaling law has been derived to visualize the relationships and to guide the choice of design parameter of the NAiMA surface 512. Line 610 illustrates the change in scale of the multiplexing, and line 620 illustrates the dynamic range of the assay.

With reference to FIGS. 7A-B, first and second micrographs illustrate a proof of concept implementation of a multiplexed digital assay with a microspot size of 300 μm, an estimated assay dynamic range of 5 orders of magnitude and up to 1600 microspots (100 spots per well, 16 wells) on a single microarray slide. FIG. 7A depicts microspots of ErbB2, FasL and IL1b, as part of 16-multiplex (16-plex) multiple discriminant analysis (MDA). FIG. 7B depicts a nanodot pattern within the boundary of a microspot.

Figure 8:
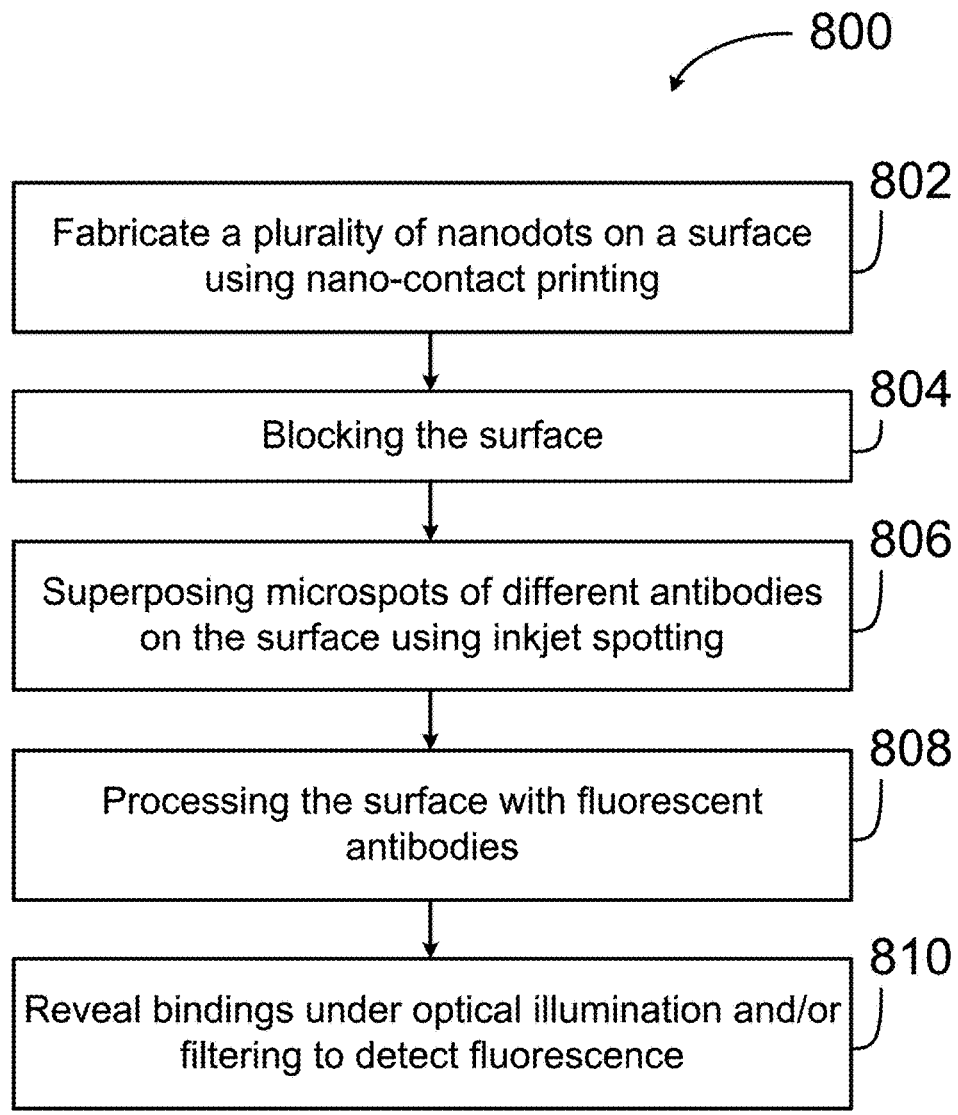
FIG. 8 is a flowchart illustrating a method for performing a nanoarray-in-microarray assay according to an embodiment.

With reference to FIG. 8, an alternative method 800 can be used to produce the assay 110. At step 802, a plurality of nanodots 514 are fabricated on a surface 512 using nano-contact printing. At step 804, the surface 512 is blocked, as shown in element 522, for example with aptamers 524 with a number of modified base pairs. At step 806, microspots 532 of different antibodies are superimposed on the surface 512 using inkjet spotting 536 to provide the NAiMA multiplexing functionality. At step 808, the surface 512 is processed with fluorescent antibodies. At step 410, bindings 550 are revealed under optical illumination and/or filtering to detect fluorescence.

Table 1 below presents a comparison of the limit of detection (LOD) and assay range obtained by multiplexed DNR and by ELISAs (a popular format of "wet-lab" type analytic biochemistry assay that uses a solid-phase enzyme immunoassay (EIA), as well as the known serum level of the measured 12 proteins.

TABLE 1

| | LOD (pg/mL) | | | Assay range (in log) | | | |
|---|---|---|---|---|---|---|---|
| | This method | Other methods R&D | Abcam | Fold difference | This method | Abcam | Difference (in log) | Known serum level (pg/mL) |
| Ang1 | 7.6 | 10.3 | 30 | 1 | 2.3 | 2.4 | −0.1 | 1.4-47 ng/mL |
| bNGF | 2.4 | na | 14 | 6 | 2.8 | 2.9 | −0.1 | 0.7 ng/mL |
| Endo | 0.4 | 30 | na | 75 | 1.8 | na | na | 3.4-56 ng/mL |
| EpCAM | 57.8 | na | na | na | 1.6 | na | na | 2 ng/mL |
| Fas | 75.4 | 20 | 3 | 0 | 1.1 | na | na | 0.7-10 ng/mL |
| FasL | 0.03 | 8.1 | 12 | 270 | 4.7 | 1.5 | 3.2 | 0.07-24 ng/mL* |
| Her2/Erb2 | 0.04 | na | 8 | 200 | 3.9 | 2.4 | 1.5 | 11 ng/mL |
| IL1b | 0.007 | 1 | 0.3 | 43 | 4.5 | 2.3 | 2.2 | 0-2.3 ng/mL* |
| IL3 | 0.3 | 7.4 | 20 | 25 | 2.5 | 2.9 | −0.3 | 0-36.5 ng/mL* |
| IL8 | 0.1 | na | 1 | 10 | 3.3 | 1.5 | 1.8 | 0-208 pg/mL* |
| MCSF | 351.4 | 9 | 5 | 0 | 1.3 | 2.9 | −1.5 | 0.07-24 ng/mL* |
| TNFa | 0.4 | 5.5 | 25 | 14 | 3.3 | 1.5 | 1.8 | 0-81 pg/mL* |

1.D. Image Analysis and Signal Extraction Algorithm

Many existing array analysis software tools are tailored for complementary DNA (cDNA) or oligonucleotide array analysis. These require inputs from the user during array segmentation and signal extraction and do not provide the particle counting feature needed for deriving information from embodiments of the invention. Accordingly, a custom image analysis and signal extraction algorithm has been established as described below. A first implementation of the algorithm has been coded via the MATLAB software suite for ease.

Figure 9C:
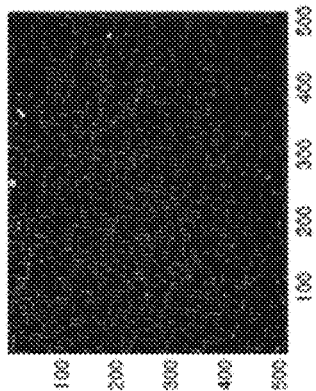
FIGS. 9A-F depicts an image analysis algorithm according to an embodiment of the invention.
Figure 9F:
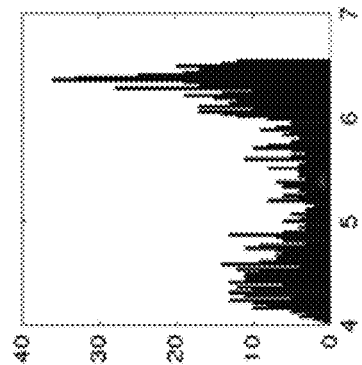
Figure 9B:
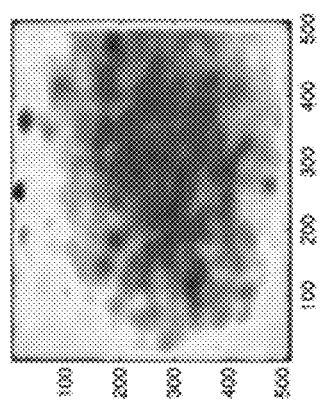
Figure 9E:
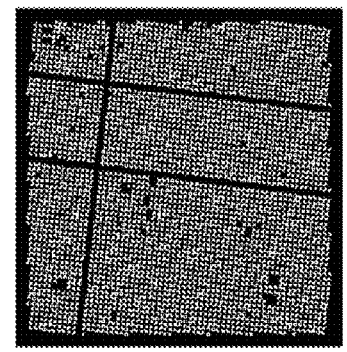
Figure 9A:
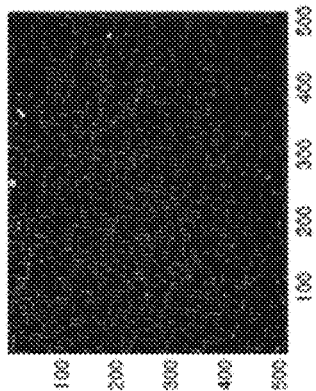

With reference to FIGS. 9A-F, the image analysis and signal quantification of a digital assay according to a tool according to an embodiment of the invention is depicted. FIG. 9A represents an original image with varying global background. FIG. 9B represents a Gaussian blurred image of the original image in first image 510 in order to highlight any background gradient (blurring essentially removes high frequency content in the image leaving low frequency content). FIG. 9C represents a normalized image after gradient subtraction, for example subtraction of the image of FIG. 9B from the image of 9A, and after an adjustment.

Figure 9D:
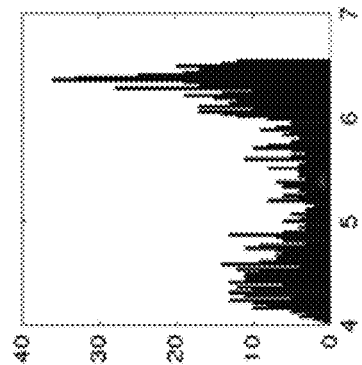

FIG. 9D represents the center of every spot fitted with a 2D Gaussian. FIG. 9E represents the spots identified on the nanoarray grid from which intensity data is extracted. FIG. 9F depicts a histogram of log-transformed dot intensity of an image, from which a threshold (asterisk) is determined, and thereafter dots with dot intensity above the threshold are counted.

1.E. Demonstration of Using NAiMA Surface to Capture Single Biomolecular Entities Exosomes are nanometer-sized vesicles secreted in large amount by cancer cells, and contain molecular composition specific to their parental cells. Accordingly, exosomes can be used to identify different types of cancers. Since tumors are highly heterogeneous in terms of cell composition and state of cells that make up the tumor, exosomes are expected to exhibit the same heterogeneity and accordingly current exosome analysis measure only average values of exosome populations. However, the heterogeneity of the exosomes, which might represent a fingerprint of their parental cells are therefore lost, and by extension, information about the heterogeneity of the cancer cell population is lost as well.

Thus, according to an embodiment of the invention, an analysis platform can be produced to establish the difference in molecular composition on exosomes of different origins, to study the heterogeneity within exosomes populations, and to identify exosomes signatures specific to cancer cell types.

Figure 10C:
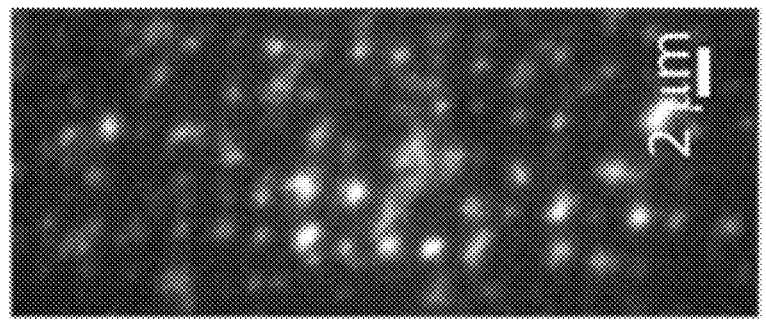
FIGS. 10A-C depicts an example nanoarray-in-microarray (NAiMA) assay according to an embodiment of the invention.
Figure 10B:
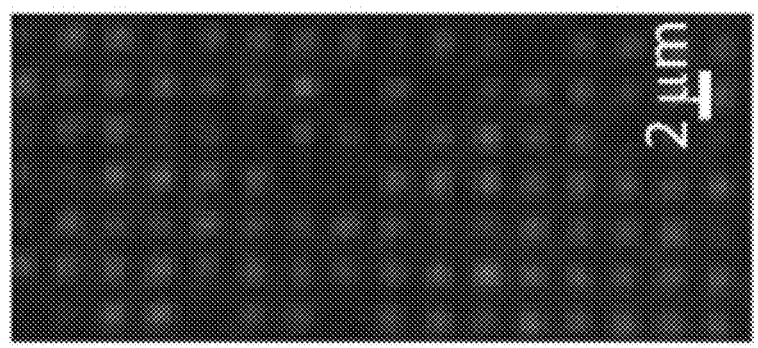
Figure 10A:
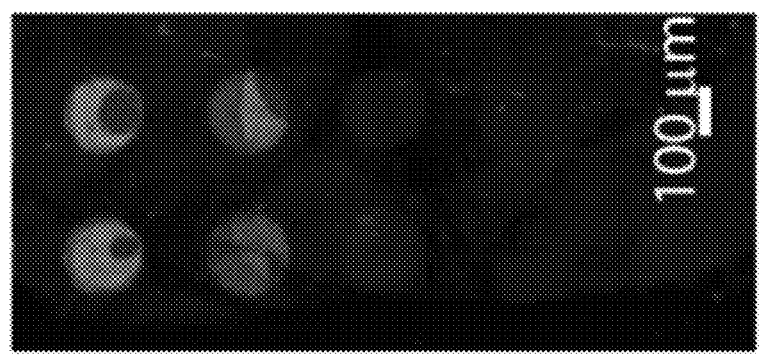

Accordingly, with reference to FIGS. 10A-C, the NAiMA platform according to an embodiment of the invention is employed for capture and detection of individual exosomes. In FIG. 10A, experimental results for the capture and detection of exosomes by anti-CD63 and anti-EGFR, respectively, on a microarray are illustrated. In FIG. 10B, a nanoarray of anti-CD63 showing 100 nm nanospots is illustrated. In FIG. 10C, exosomes captured on an anti-CD63 nanoarray according to an embodiment of the invention are depicted, as detected by anti-EGFR showing different signal intensity for each nanospot. Accordingly, certain embodiments of the invention provide for single molecule detection with noise rejection beyond the levels of prior art single molecule assays.

Figure 11:
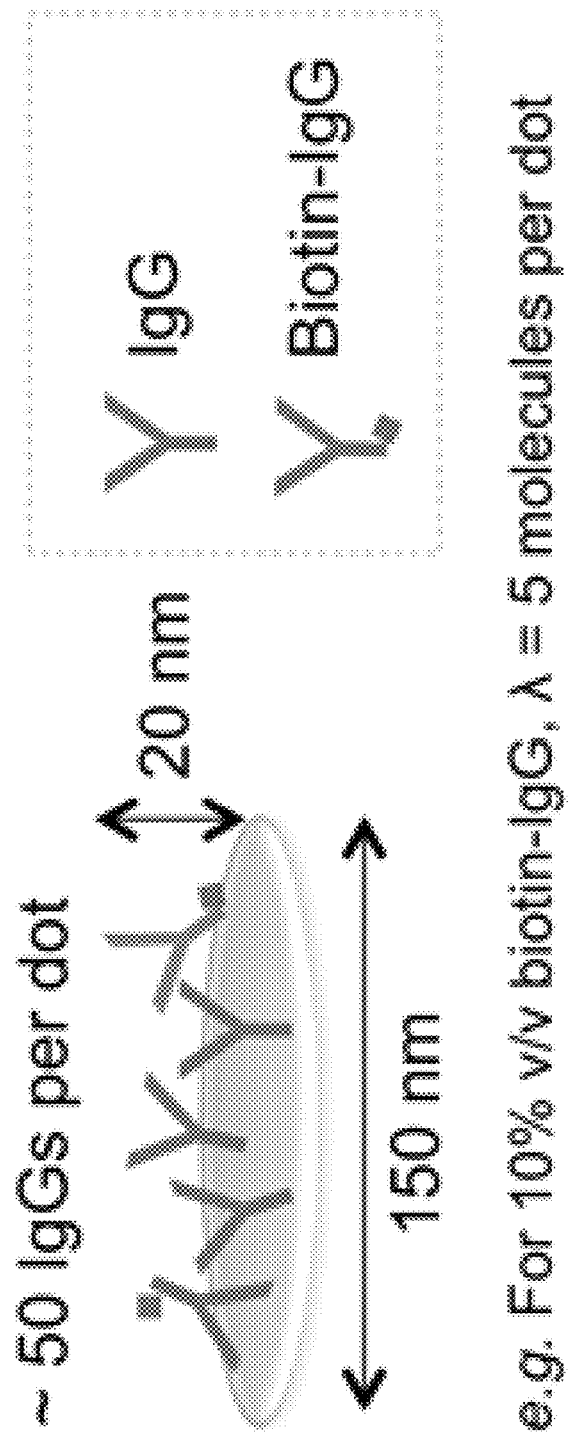
FIG. 11 is a schematic drawing of an assay according to an embodiment.
Figure 12A:
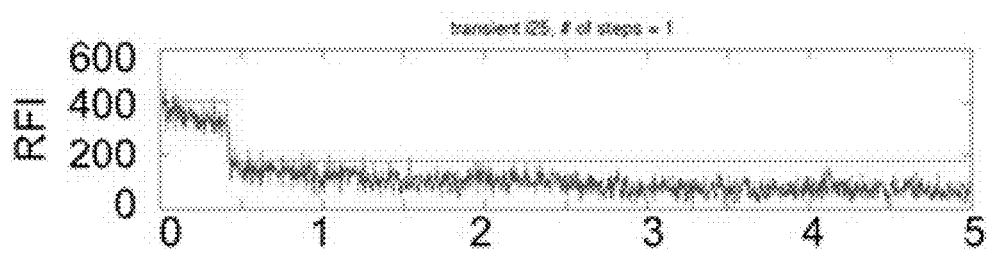
FIGS. 12A-C, 13A-D, and 14 depict experimental results for single molecule binding on nanodots according to an embodiment of the invention.
Figure 12B:
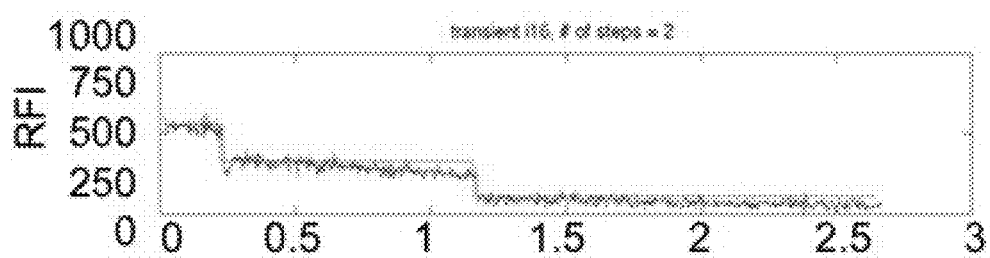
Figure 12C:
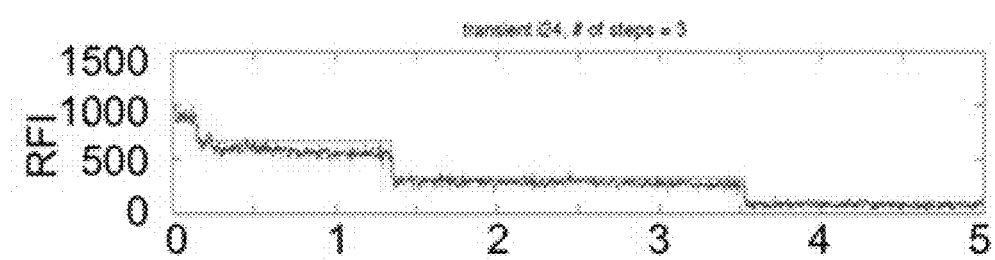
Figure 13A:
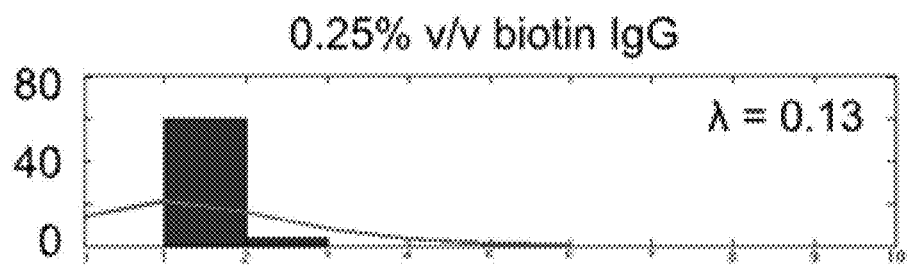
Figure 13B:
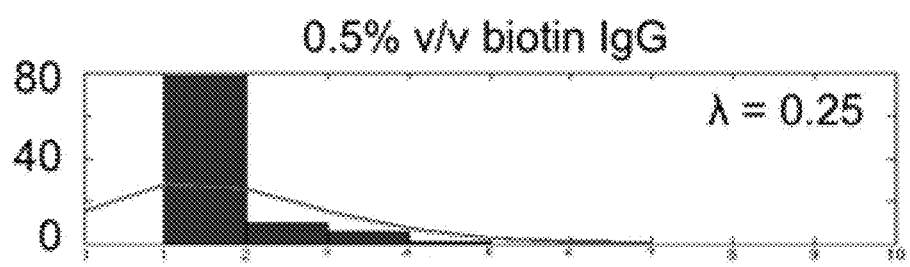
Figure 13C:
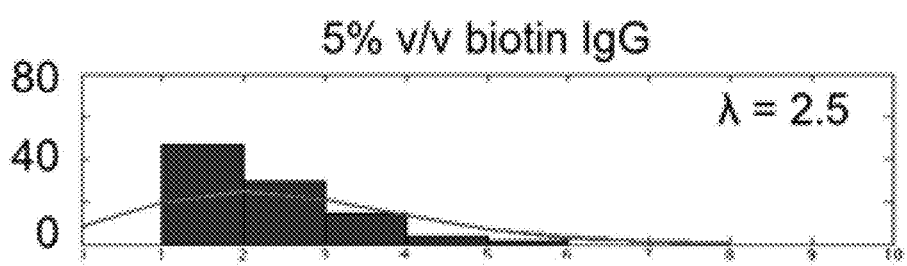
Figure 13D:
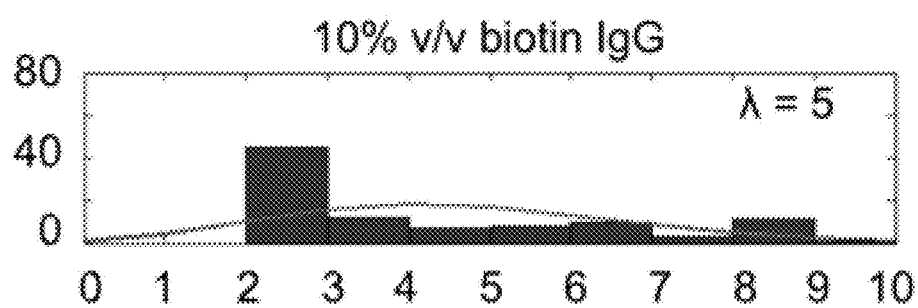

With reference to FIG. 11, a schematic drawing of an assay with ~50 biotinylated IgGs on a nanodot of 150 nm is shown. This assay can be used for validation of single molecule binding on nanodot using photobleaching. With reference to FIGS. 12A-C, example transient responses of fluorescence decay on a single nanodot are depicted, showing a step-wise characteristic. The number of steps indicates the number of molecules per dot. FIG. 12A shows an embodiment with an i25 transient and one step; FIG. 12B shows an embodiment with an i16 transient, and two steps; FIG. 12C shows an embodiment with an i24 transient, and three steps.

Figure 14:
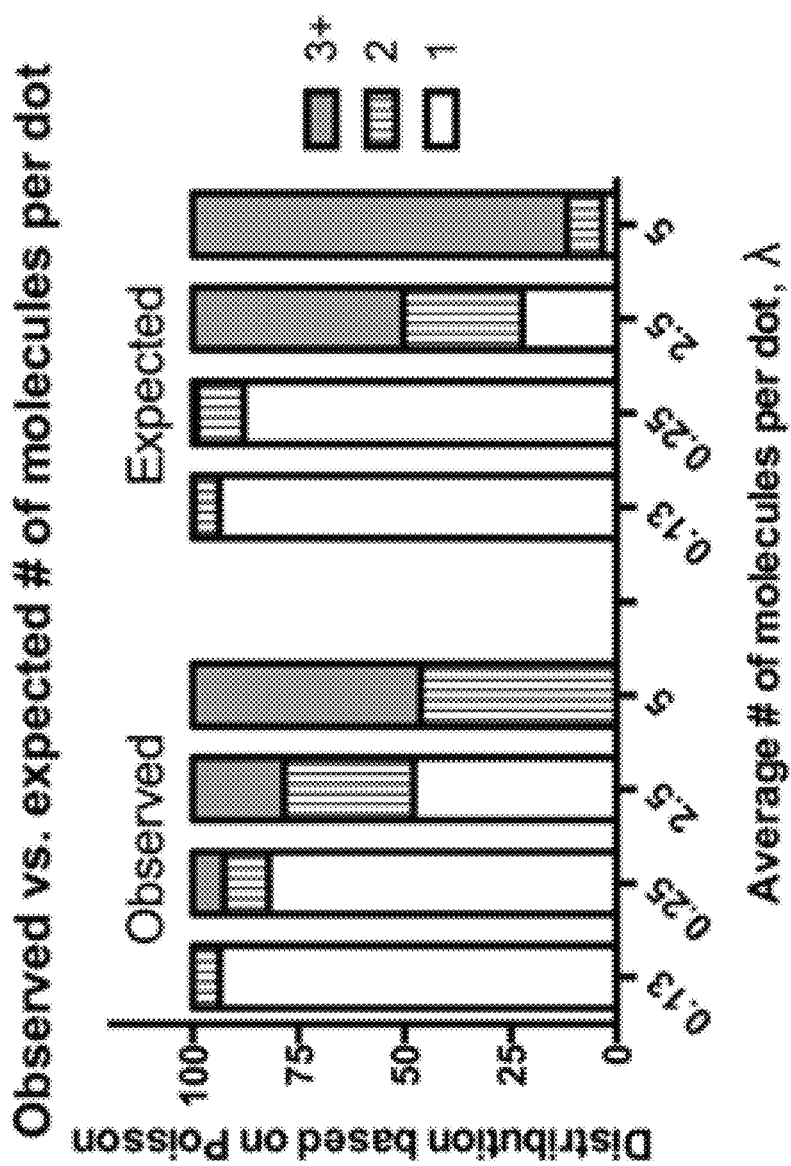

With reference to FIGS. 13A-D, histograms of the number of molecules per dot when the expected average molecule per dot is 5, 2.5, 0.25, and 0.13 are shown. In each case, 100 traces were analyzed. With reference to FIG. 14, observed distributions of one, two, and three and more molecules per dot are shown and compared with expected distribution calculated based on Poisson statistics.

B. General Purpose and Commercial Applications:

The embodiments of the invention presented supra in respect of DNR with noise rejection arising from non-specific binding and nanoarray-in-microarray (NAiMA) may form the basis for a wide range of general purpose consumer applications, commercial applications, and medical applications. These innovations allow for molecular diagnostics exploiting highly specialized and ultra-sensitive assays with potential applications including, but not limited, novel biomarker discovery and early disease diagnosis. Molecular diagnostics (MDx) is one of the fastest growing segments in the in vitro diagnostic (IVD) industry wherein the embodiments of the invention improve the assay performance through addressing noise rejection, a feature that no existing technologies address, and an innovative micro-/nano-patterned assay surface for highly multiplexed concurrent analysis. Thus, the concepts presented and described supra in respect of embodiments of the invention may also be applied to clinical tests by using known biomarkers and exiting molecule diagnostic targets.

For future commercialization as a diagnostic test, the embodiments disclosed herein provide an integrated solution comprising an assay, with analysis software that can transform the raw data to useful test results. The assay employed may be selected in dependence upon a variety of factors including, but not limited to, the target market and target cost. For example, a low cost assay system may exploit silver assay labelling nanoparticles whilst a higher cost assay system may exploit fluorescent assay labeling molecules in conjunction with a solid state light source(s) and a CCD array disposed adjacent the assay in predetermined relationship providing megapixel images. More flexible higher end laboratory systems may exploit fluorescent or silver nanoparticles labelling with an imaging system, such as a TIRF microscope and dark field (DF) microscope respectively.

Although the descriptions and embodiments of the invention presented supra relate to the use of antibodies for providing the affinity based binding of target molecule(s), other affinity binders may be exploited discretely or in combination with each other and antibodies within a multiplexed analysis. Such affinity binders including but not limited to, natural binders, artificial binders, recombinant binders such as proteins, nucleic acids, and aptamers.

Although the descriptions and embodiments of the invention presented supra demonstrated an application of using nanoarrays to capture single exosomes, nanometer vesicles secreted by cells, to study the diversity of the exosome population, that other single biomolecular entities can be captured using the methodologies and devices according to embodiments of the invention.

Although embodiments of the invention have been described with respect to nano-contact printing and inkjet spotting, dispersal and deployment of binders, antibodies, markers, etc. may be provided via one or more other techniques and technologies known to those of skill in the art either alone or in combination. Such techniques may include, but not be limited to, silicon micromachining, silicon nanofluidics, LIGA (Lithographie, Galvanoformung, Abformung in German referring to Lithography, Electroplating, and Molding, clam-shell assemblies). Exploiting such technologies NAiMA assays and/or DNR with noise reduction solutions addressing assays ranging from disposable consumer and/or point-of-care solutions through to clinical/surgery systems and laboratory systems can be considered.

Additionally, the dimensions of the nanodots, their spacing, the number per block, the geometry of the block etc. may be varied without departing from the scope of the invention.

Although the embodiments of the invention are described and depicted exploiting affinity binders formed through liquid contact printing, ink jet printing, etc., the affinity binders may be formed through other processes with the affinity binder in gaseous, liquid, or solid form or a combination thereof such as processing a low temperate affinity binder in solid form but employing it in the assay in liquid form. Moreover, a variety of semiconductor, microelectronic, and nanostructure manufacturing techniques may be employed. Further, although "nanodots" have been described and depicted which are circular and according to their volume, liquid properties hemispherical or flat that other geometries may be employed include nanorods etc. through patterning of and/or processing of and/or depositing onto the substrate prior to affinity binder positioning with a material suppressing the binder nanodots adhering to the surface.

Although microscopy has been described and depicted for performing the optical imaging prior to analysis and that a CCD has been described for low cost solutions that other optical image acquisition systems including, but not limited to digital cameras, photographic film, digital video cameras, optical scanners, flat-bed scanners etc. may employed according to their capabilities and the dimensions of the NAiMA.

Extensions of the concepts and methodologies presented supra may include, but not be limited to: integration with microfluidics and/or nanofluidics and analysis of DNA, by using two complementary probes, one to capture DNA, and one to detect the captured strands. Additionally, assays may be performed on a variety of substrates including, but not limited to, glass, silicon, polymer, and plastic. Assays may be performed using random nanoarrays as capture spots instead of regular nanoarrays, using nanoparticles as capture spots, and with detection antibodies conjugated to nanoparticles. Moreover, integration of the assay for compatibility with consumer electronics and/optics such as DVD/CD/BluRay technology which can read at high densities, e.g. 150 nm "pits" spaced 320 nm apart.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

The invention claimed is:

1. A method for performing an assay, comprising:
   fabricating a plurality of nanodots on a surface having at least one affinity binder;
   applying a microspot on a predetermined region of the surface to superimpose the microspot over a number of the nanodots to form a nanoarray-in-microarray having the number of the nanodots within a perimeter of the microspot, the microspot comprising at least one antibody of a plurality of antibodies;
   performing an affinity-binding assay process on the surface;
   acquiring at least one optical image of the number of nanodots within the microspot; and
   performing an image analysis on the at least one optical image to identify bindings on individual ones of the number of nanodots.

2. The method of claim 1, wherein the predetermined region of the array of nanodots is defined by blocking the surface to define the predetermined region with predetermined geometry.

3. The method of claim 2, wherein blocking the surface comprises applying at least one aptamer having a predetermined number of modified base pairs.

4. The method of claim 1, wherein fabricating the plurality of nanodots comprises nano-contact printing the plurality of nanodots.

5. The method of claim 1, wherein applying the microspot comprises inkjet spotting the microspot.

6. The method of claim 1, wherein performing the image analysis comprises performing spatial rejection of non-specific bindings by at least excluding antibodies of the plurality of antibodies outside the microspot.

7. The method of claim 1, wherein performing the affinity-binding assay process comprises performing one or both of:
   a silver-enhanced sandwich immunoassay process; and
   an immunoassay process employing at least one of a fluorescent marker and a photoluminescent marker.

8. The method of claim 1, wherein performing an image analysis comprises:
   generating a low frequency content image from the acquired optical image;
   subtracting the low frequency content image from the optical image to generate a normalized image;
   fitting a 2D Gaussian at the centre of each of a plurality of microspots in the normalized image;
   applying a spot mask to extract data relating to the plurality of microspots; and
   extracting an intensity reading for at least some of the number of nanodots within the optical image based on the plurality of microspots.

9. The method of claim 8, wherein performing an image analysis further comprises:
   establishing a threshold within the extracted intensity reading; and
   obtaining a count of nanodots with an intensity reading meeting a predetermined condition with respect to the threshold as instances of a binding occurrence.

10. An assay device, comprising;
    a detection surface having defined thereon a plurality of nanodots each having at least one affinity binder; and
    a microspot applied on a predetermined region of the detection surface such that the microspot is superimposed over a number of the nanodots to form a nanoarray-in-microarray having the number of the nanodots within a perimeter of the microspot, the microspot comprising at least one antibody of a plurality of antibodies.

11. The assay device of claim 10, further comprising at least one aptamer applied to the detection surface to define the predetermined region with predetermined geometry, the at least one aptamer having a predetermined number of modified base pairs.

12. The assay device of claim 10, wherein the plurality of nanodots are fabricated by nano-contact printing.

13. The assay device of claim 10, wherein the microspot is fabricated by inkjet spotting.

14. The assay device of claim 10, wherein the nanodots are configured to perform spatial rejection of non-specific bindings as part of an image analysis process by at least excluding antibodies of the plurality of antibodies outside the microspot.

15. The assay device of claim 10, wherein a spacing between the plurality of nanodots is 2 μm.

16. The assay device of claim 10, wherein a diameter of the microspot is between 100 μm and 800 μm.

17. A method for estimating a protein concentration in a sample solution, comprising:
  forming a nanoarray-in-microarray by immobilizing nanodots of capture antibodies mixed with fluorescently-labeled detection antibodies on a microarray slide using nano-contact printing to superimpose a nanoarray of the nanodots on a predetermined region of the microarray slide having microspots forming a microarray, wherein a number of the nanodots are disposed within a perimeter of one or more of the microspots of the microarray;
  performing a sandwich assay with the nanoarray-in-microarray by sequentially incubating the sample solution with the fluorescently-labelled detection antibodies;
  imaging results of the assay to acquire a plurality of two-colour fluorescent images;
  overlaying the acquired two-colour fluorescent images to reveal at least one co-localized spot; and
  performing an image analysis algorithm to count the at least one co-localized spot to estimate the protein concentration.

18. The method of claim 17, wherein performing a sandwich assay comprises performing a silver-enhanced sandwich immunoassay.

19. The method of claim 17, wherein imaging the results of the assay comprises imaging the assay with a total internal reflection fluorescent microscope.

20. The method of claim 17, wherein performing an image analysis algorithm comprises revealing bindings under a dark field microscope.

* * * * *